(12) United States Patent
Patil et al.

(10) Patent No.: US 10,995,312 B2
(45) Date of Patent: May 4, 2021

(54) BIOMANUFACTURING APPARATUS

(71) Applicant: Global Life Sciences Solutions USA LLC, Marlborough, MA (US)

(72) Inventors: Haresh Digambar Patil, Bangalore (IN); Praveen Paul, Bangalore (IN); Manish Uddhaorao Choudhary, Bangalore (IN); Pradeep Kumar, Bangalore (IN); Anoop Bhargav, Bangalore (IN); Sebastian John, Bangalore (IN); Nivedita Phadke, Bangalore (IN); Manoj Ramakrishna, Bangalore (IN)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 410 days.

(21) Appl. No.: 15/755,084

(22) PCT Filed: Aug. 25, 2016

(86) PCT No.: PCT/EP2016/070075
§ 371 (c)(1),
(2) Date: Feb. 25, 2018

(87) PCT Pub. No.: WO2017/032829
PCT Pub. Date: Mar. 2, 2017

(65) Prior Publication Data
US 2019/0017011 A1 Jan. 17, 2019

(30) Foreign Application Priority Data

Aug. 25, 2015 (IN) .......................... 2632/DEL/2015
Oct. 19, 2015 (GB) ...................................... 1518426

(51) Int. Cl.
*C12M 1/00* (2006.01)
*C12M 3/06* (2006.01)
(Continued)

(52) U.S. Cl.
CPC ............ *C12M 41/14* (2013.01); *C12M 23/04* (2013.01); *C12M 23/48* (2013.01); *C12M 27/16* (2013.01); *C12M 29/00* (2013.01); *C12M 41/48* (2013.01)

(58) Field of Classification Search
CPC ... C12M 41/14; C12M 27/16; B01L 2200/025
See application file for complete search history.

(56) References Cited

U.S. PATENT DOCUMENTS

| 5,882,918 A | 3/1999 | Goffe |
| 2002/0140324 A1* | 10/2002 | Butts ..................... C12M 41/14 312/209 |

(Continued)

FOREIGN PATENT DOCUMENTS

| CN | 102807952 A | 12/2012 |
| CN | 204848846 U | 12/2015 |

(Continued)

OTHER PUBLICATIONS

International Search Report and the Written Opinion of the International Searching Authority, or the Declaration from International Appl. No. PCT/EP2016/070075, dated Nov. 14, 2016.

(Continued)

*Primary Examiner* — Jonathan M Hurst
(74) *Attorney, Agent, or Firm* — Eversheds Sutherland (US) LLP (57) ABSTRACT

Disclosed is biomanufacturing apparatus 1 comprising a housing 20 including top 22 and bottom 24 faces which allow stacking of plural housings, an access door 25 at a front side of the housing, a substantially enclosed bioreactor chamber 30 inside the housing accessible via the door, and a further substantially enclosed region 36 inside the housing containing electrical parts and/or electronic control components, the chamber 30 including: a tray 40 for supporting a bioreactor, a tray support 45 including a mechanism 44,47

(Continued)

for rocking the tray in use; at least a fluid handling portion 48,49 of at least one fluid pump device 54/58; and at least one connection 43 for connecting to a conduit and/or path for carrying fluids, gas and/or electricity.

17 Claims, 8 Drawing Sheets

(51) Int. Cl.
     *C12M 1/36*      (2006.01)
     *C12M 1/12*      (2006.01)
     *C12M 3/00*      (2006.01)

(56) References Cited

U.S. PATENT DOCUMENTS

| | | | |
|---|---|---|---|
| 2004/0114316 A1* | 6/2004 | Carter | B01L 1/02 361/679.29 |
| 2009/0111179 A1* | 4/2009 | Hata | C12M 23/14 435/394 |
| 2011/0315783 A1* | 12/2011 | Baker | C12M 41/14 236/3 |
| 2012/0258441 A1* | 10/2012 | Gebauer | C12M 23/14 435/3 |

FOREIGN PATENT DOCUMENTS

| | | |
|---|---|---|
| EP | 2607474 A1 | 6/2013 |
| JP | 2006-204186 A | 8/2006 |
| JP | 2007-174982 A | 7/2007 |
| WO | 2011078773 A1 | 6/2011 |
| WO | 2013135817 A1 | 9/2013 |
| WO | 2017032829 A1 | 3/2017 |

OTHER PUBLICATIONS

Great Britain Search Report from GB Appl. No. GB1518426.0, dated Jul. 26, 2016.
Celltainer Biotech, "Cell-tainer single-use bioreactor for cell cultures—CM2SCEU/CM2SCUS", celltainer.com, [online], Available from: http://celltainer.com/wp-content/uploads/2015/01/cell-culture.pdf [Accessed Jul. 22, 2016] See particularly System Specifications.
Japanese Office Action for JP Application No. 2018-510070 dated Jun. 8, 2020 (8 pages with English translation).
Chinese Office Action for CN Application No. 201680062248.8 dated Dec. 3, 2020 (22 pages with English translation).

\* cited by examiner

FIG. 9

BIOMANUFACTURING APPARATUS

FIELD OF THE INVENTION

The present invention relates to biomanufacturing apparatus, for example for cell culturing. In particular, the invention relates to bioreactor apparatus in the form of single instruments, and plural instruments arranged into a biomanufacturing system for optimising the usage of laboratory and cell culturing space for biomanufacturing.

BACKGROUND OF THE INVENTION

Cell culture, for example the culture of mammalian, bacterial or fungal cells, may be carried out to harvest the living cells for therapeutic purposes and/or to harvest biomolecules, such as proteins or chemicals (e.g. pharmaceuticals) produced by the cells. As used herein, the term "biomolecule" can mean any molecule, such as a protein, peptide, nucleic acid, metabolite, antigen, chemical or biopharmaceutical that is produced by a cell or a virus. Herein, the term biomanufacturing is intended to encompass the culturing or multiplication of cells, and the production of biomolecules. The term bioreactor is intended to encompass a generally enclosed volume capable of being used for biomanufacturing.

The cells are generally grown in large scale (10,000 to 25,000 litre capacity) bioreactors which are sterilisable vessels designed to provide the necessary nutrients and environmental conditions required for cell growth and expansion. Conventional bioreactors have glass or metal growth chambers which can be sterilized and then inoculated with selected cells for subsequent culture and expansion. Media within the growth chambers are often agitated or stirred by the use of mechanical or magnetic impellers to improve aeration, nutrient dispersal and waste removal.

In recent years, there has been a move towards 'single use' bioreactors which offer smaller batch sizes, greater production flexibility, ease of use, reduced capital cost investment and reduced risk of cross-contamination. These systems can also improve the efficiency of aeration, feeding and waste removal to increase cell densities and product yields. Examples include WAVE™ bags (GE Healthcare) mounted on rocking platforms for mixing, to the introduction of stirred-tank single-use vessels such as those available from Xcellerex Inc (GE Healthcare). With the advent of 'personalised medicine', autologous cell therapies requiring many small batches of cells to treat patients with unique cell therapies has become important.

Manufacturing facilities, such as tissue culture laboratories, for the production of cells and biomolecules, have traditionally been custom designed and carried out in clean environments to reduce the risk of contamination. Such facilities are costly to run and maintain and also to modify if priorities or work demands change. Work stations for maintaining or harvesting the cells within the bioreactors require a specific 'footprint' which occupies a significant floor space in the culture laboratory. As the workstations spend much of their time unattended, while the cells are growing in the bioreactors, the laboratory space is not efficiently or effectively used.

An improvement is proposed in WO 2014122307, wherein the laboratory space required for cell culture is reduced by the provision of customised workstations and storage bays for bioreactors, on which, conventional WAVE type bioreactors and ancillary equipment can be supported. Large supporting frameworks are required for that equipment.

U.S. Pat. No. 6,475,776 is an example of an incubator for cell culture dishes, which has a single incubator housing and multiple shelves, however this type of equipment is not suitable for housing bioreactors.

What is needed is the ability to stack multiple bioreactors one on top of another, closely spaced side by side, in a system that is simple to load, operate and maintain. Ideally such bioreactors should be capable of tradition fed batch manufacturing where cells are cultured typically over 7 to 21 days, as well as perfusion type manufacturing where cells can be cultured for longer periods, but waste products are continually or regularly removed, and biomolecules may be harvested.

SUMMARY OF THE INVENTION

The invention provides an arrangement according to claim 1 having preferred features defined by claims dependent on claim 1. The invention provides also a system and method according to according to claims 16 and 17 respectively.

The invention extends to any combination of features disclosed herein, whether or not such a combination is mentioned explicitly herein. Further, where two or more features are mentioned in combination, it is intended that such features may be claimed separately without extending the scope of the invention.

BRIEF DESCRIPTION OF THE DRAWINGS

The invention can be put into effect in numerous ways, illustrative embodiments of which are described below with reference to the drawings, wherein.

The invention, together with its objects and the advantages thereof, may be understood better by reference to the following description taken in conjunction with the accompanying drawings, in which like reference numerals identify like elements in the Figures.

Figures 1A, 1B:
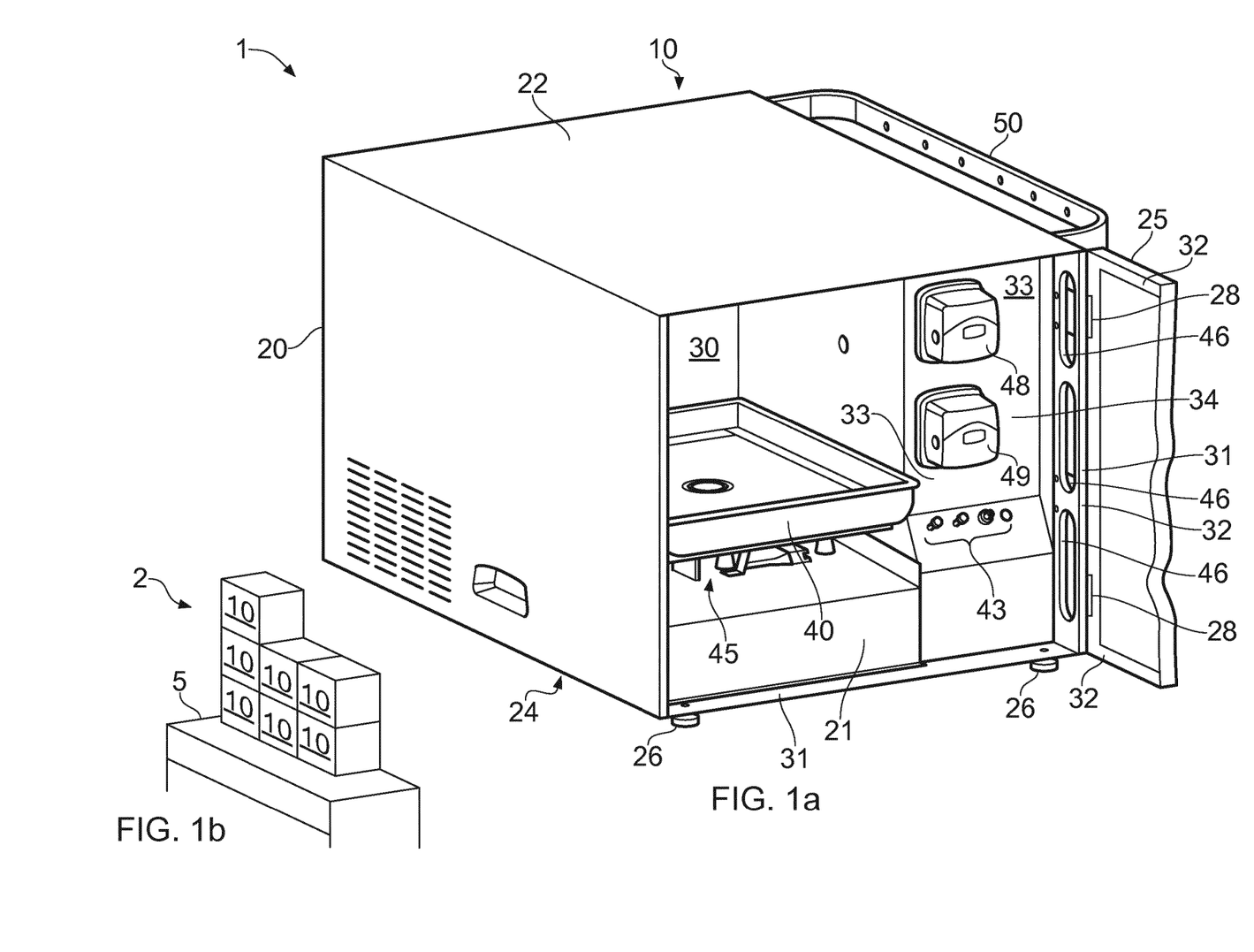
FIG. 1a shows a pictorial view of an embodiment of biomanufacturing apparatus.
FIG. 1b shows the apparatus of FIG. 1a stacked to form a biomanufacturing system 2.

Referring to FIG. 1a there is shown biomanufacturing apparatus 1 including a generally self-contained instrument 10 which includes a generally cuboid or box-shaped housing 20 having generally flat upper and bottom sides 22 and 24. The bottom side includes four adjustable height feet 26, only two of which are visible in FIG. 1a. The box shaped housing allows stacking of plural instruments to form a biomanufacturing system. In practice, for convenience, the stack will be two or three high on a benchtop 5, as schematically illustrated in FIG. 1b, although there is no reason why the stack could not be higher. The instrument also includes a door 25, shown open and cut away for in order to shown the remaining parts of the instrument more clearly. The door is hinged at hinges 28 to the front vertical edge of the housing, so that it opens about a vertical hinge axis to expose or enclose an insulated chamber 30 inside the housing 20. The chamber 30 is sealed when the door is closed by an elastomeric seal 32 extending around the whole periphery of the inner face of the door and cooperating with a seal face 31 extending in a complementary manner around the front edges of the housing 20. No light enters the chamber 30 when the door 25 is closed. This negates light effects on the cell culture.

The chamber 30 has a main chamber 35 and an antechamber 33 leading to the main chamber 35. The main chamber includes a bioreactor tray 40, supported by a rocking tray support 45 described in more detail below. The rocking mechanism is protected by a cover plate 21. The antechamber 33 includes a panel 34 supporting two peristaltic pumps only the fluid handling heads 48 and 49 of which extend into the antechamber 33, the electrical parts of which are behind the panel 34. The panel also includes connections 43 described in more detail below. The antechamber 33 includes openings 46 defining a route for conduits extending to an external storage area which includes a bag hanging rack 50.

Figure 2:
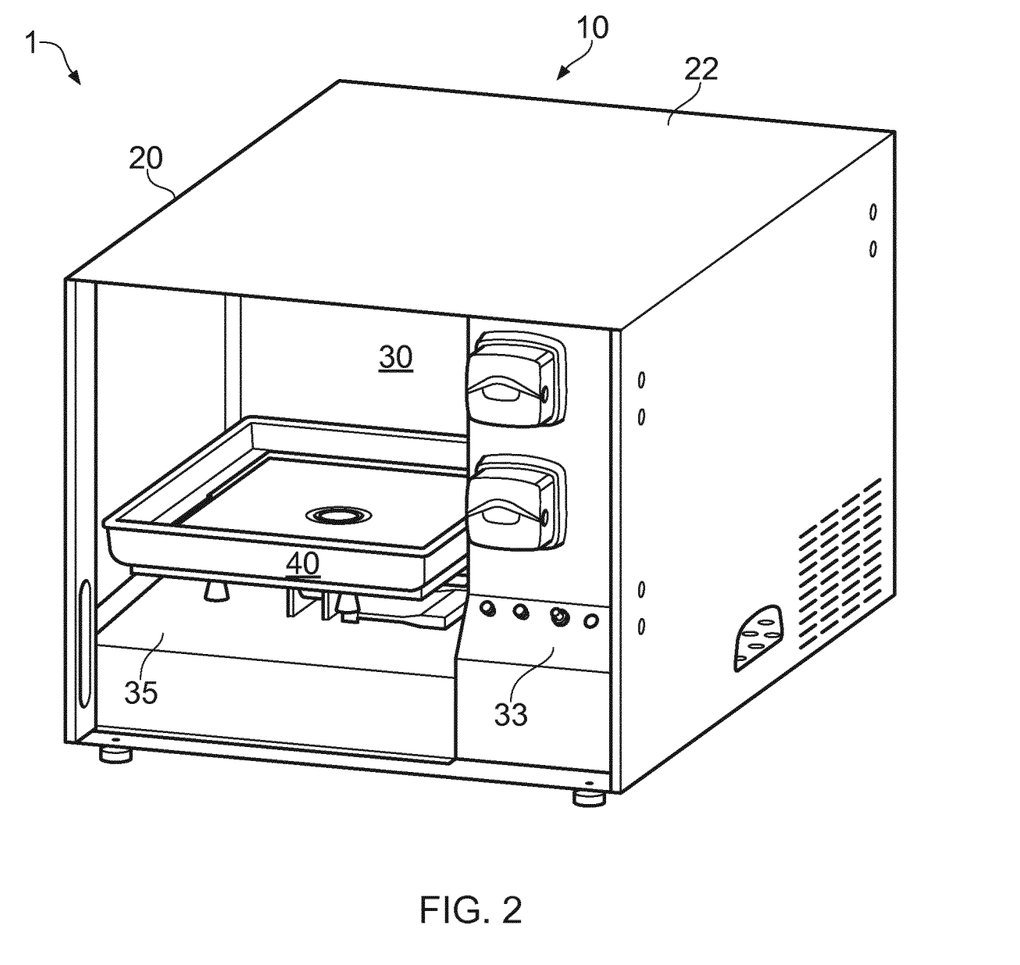
FIG. 2 shows a different pictorial view of the apparatus shown in FIG. 1.

FIG. 2 is a different view of the instrument 10 shown in FIG. 1, with the door 25 and bag rack removed 50, in order to show the remaining parts of the instrument more clearly.

Figure 3:
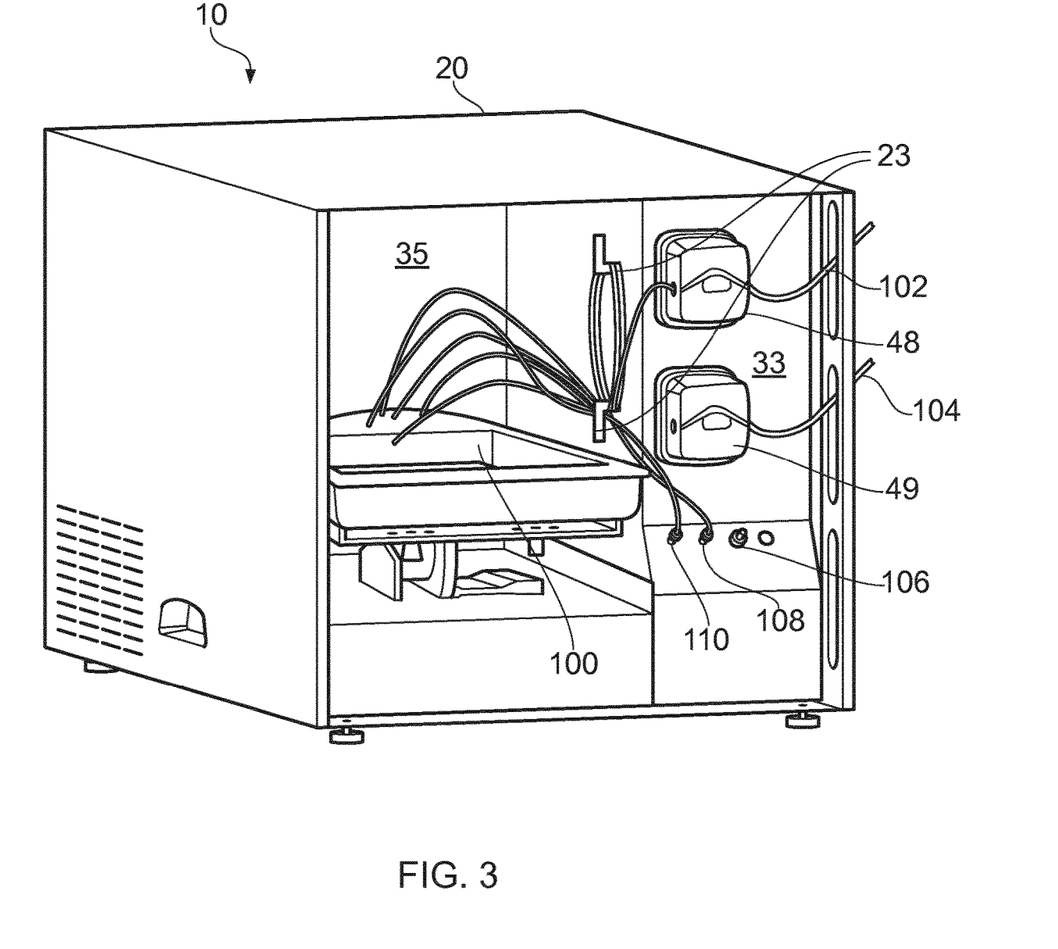
FIG. 3 shows another pictorial view of the apparatus shown in FIG. 1, including a bioreactor loaded inside the apparatus.

FIG. 3 shows the instrument 10 of FIGS. 1 and 2, but loaded with a bioreactor 100, in this instance, in the form of a flexible bag 100, as well as various paths linking the bioreactor to the instrument, including: a fluid supply conduit 102 feeding the bioreactor with a known mixture of fluids to promote cell growth via the peristaltic pump head 48, a fluid removal conduit 104 for drawing off fluids from the reactor for the purpose of removing waste components expressed by cells in the bioreactor via a filter incorporated in the bag 100 and via the peristaltic pump head 49; a gas feed conduit 106; and paths, for example electrically conductive paths 106, 108 and 110 for example electrical wires, for various sensors within or adjacent the bioreactor, for example a pH sensor, and a dissolved oxygen (DO) sensor. The conduits and paths can be kept in place by one or more hangers 23.

Figure 4:
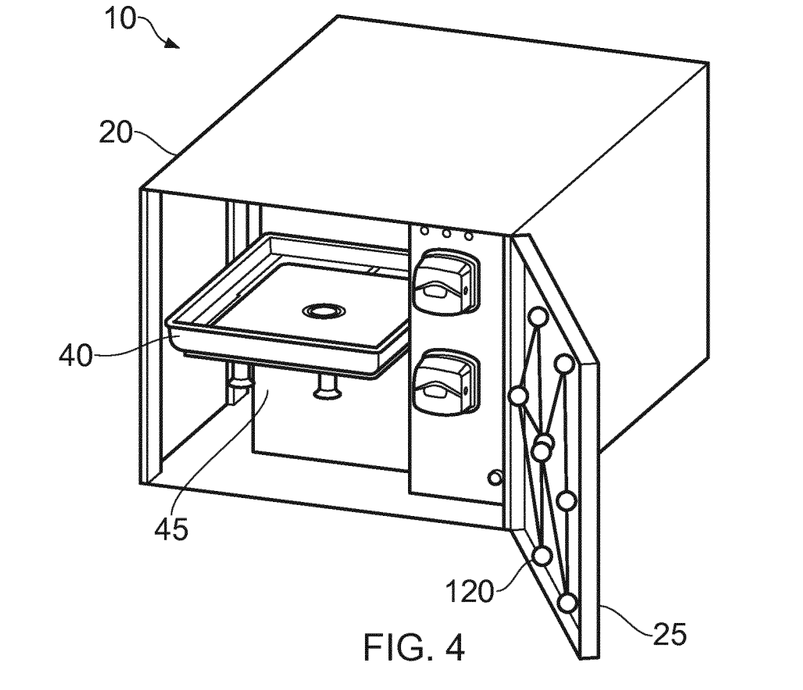
FIGS. 4 and 5 show two pictorial views of a further embodiment of biomanufacturing apparatus, in different configurations.
Figure 5:
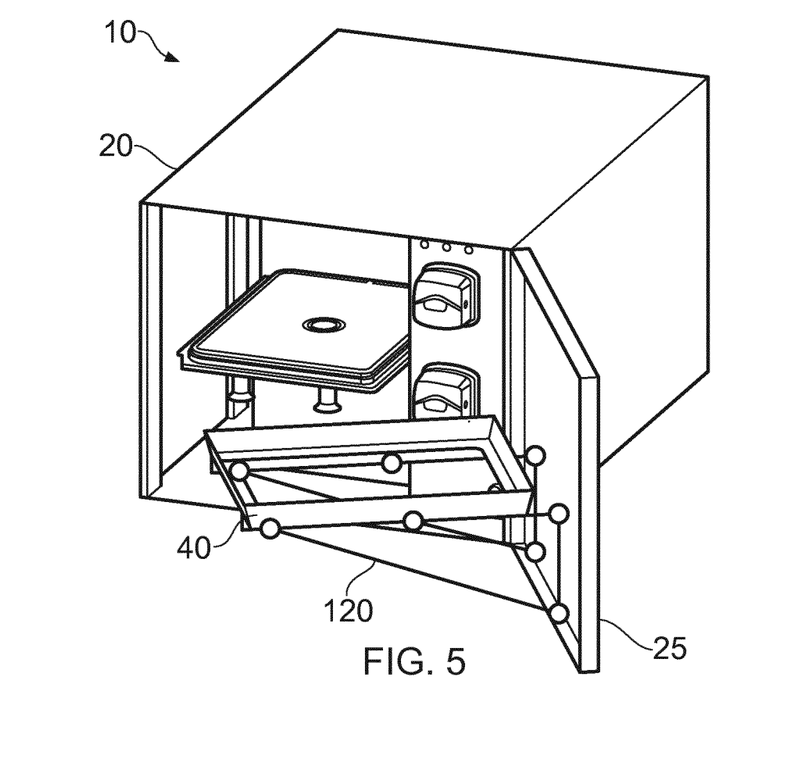

FIGS. 4 and 5 show an embodiment of the instrument 10 including the door 25. The tray 40 in this embodiment is removable from the tray support 45 by sliding motion and can rested on a collapsible stand 120, in turn hung on the hinged door 25. In use, the door 25 can be opened, the stand 120 can be dropped down, and the tray 40 (without or without a bioreactor in place) can be slid away from the support 45 and manually moved onto the stand. It will be noted that the tray 40 has an open mid-section. This open section accommodates a bioreactor, which has clips that clip onto the tray 40 sides so that the bioreactor does not fall through the middle of the tray. Returning the tray full or empty back into the chamber 30, allows the frame 120 to be folded away and the door 25 to be closed shut.

Figure 6A:
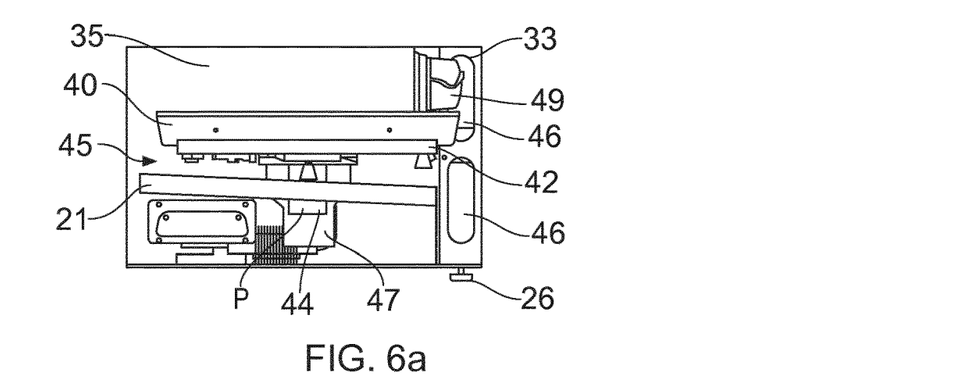
FIGS. 6a, 6b, 6c and 6d show a partial sectional view of the apparatus shown in FIGS. 1 and 2.
Figure 6B:
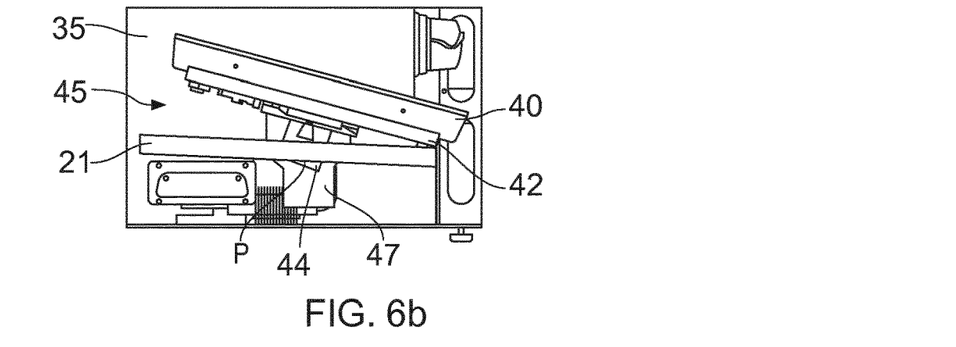
Figure 6C:
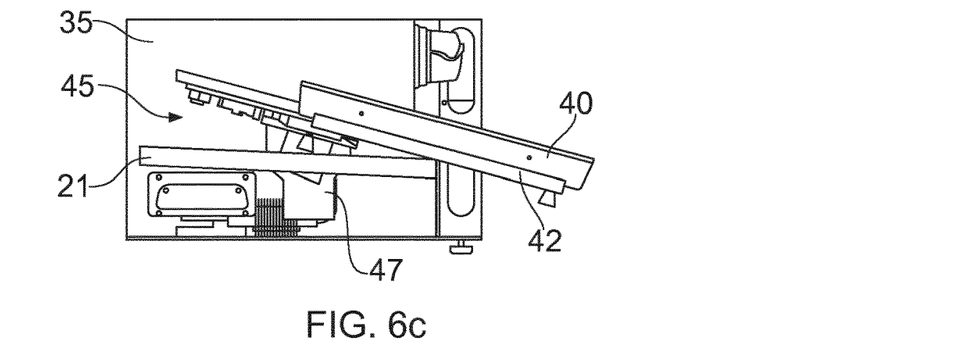
Figure 6D:
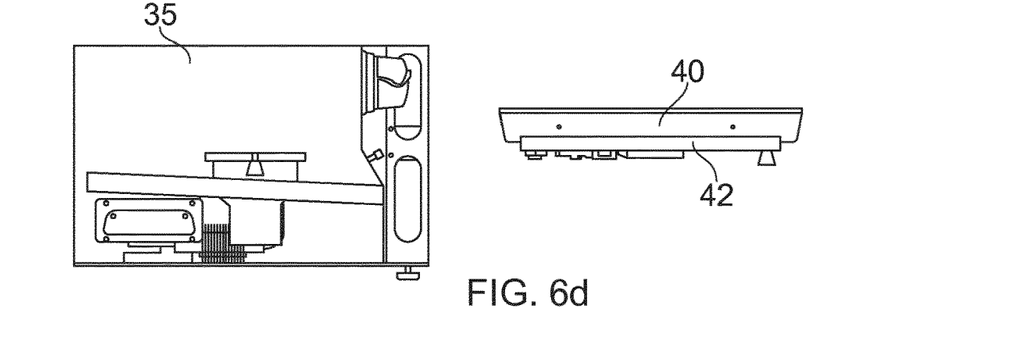

FIGS. 6a, 6b, 6c and 6d each show a sectional view of the main chamber 35 illustrated in FIGS. 1 to 3, and the components housed therein. Those components include the removable tray 40 and the rocking tray support 45. The tray support 45 is formed from an electrically heated plate 42 which is in direct contact with the bottom of a bioreactor in use, a pivotable plate holder 44 which releasably holds the heated plate and an electrical stepper motor driving rocking mechanism 47 which moves the plate holder 44 back and forth about a pivot axis P below the tray 40 through a predefined angle of about 25-35 degrees. The support 45 is controllable in use so that it stops in any position, but in particular in the forward slopping position shown in FIG. 6b, which enables the tray 40 and plate 42 to be slid forward together whilst the plate holder 44 stays in position, to a new position as illustrated in FIG. 6c, where the tray is more readily accessible for loading or unloading rather than having to remove it as shown in the embodiment of FIGS. 4 and 5. In the position shown in FIG. 6c the conduits and paths between the bioreactor and the instrument, as mentioned above, can be connected or disconnected more easily. The tray 40 and plate 42 can be removed completely as shown in FIG. 6d, for example, for cleaning purposes. A cover plate 21 protects the motor and other electrical parts.

Figure 7:
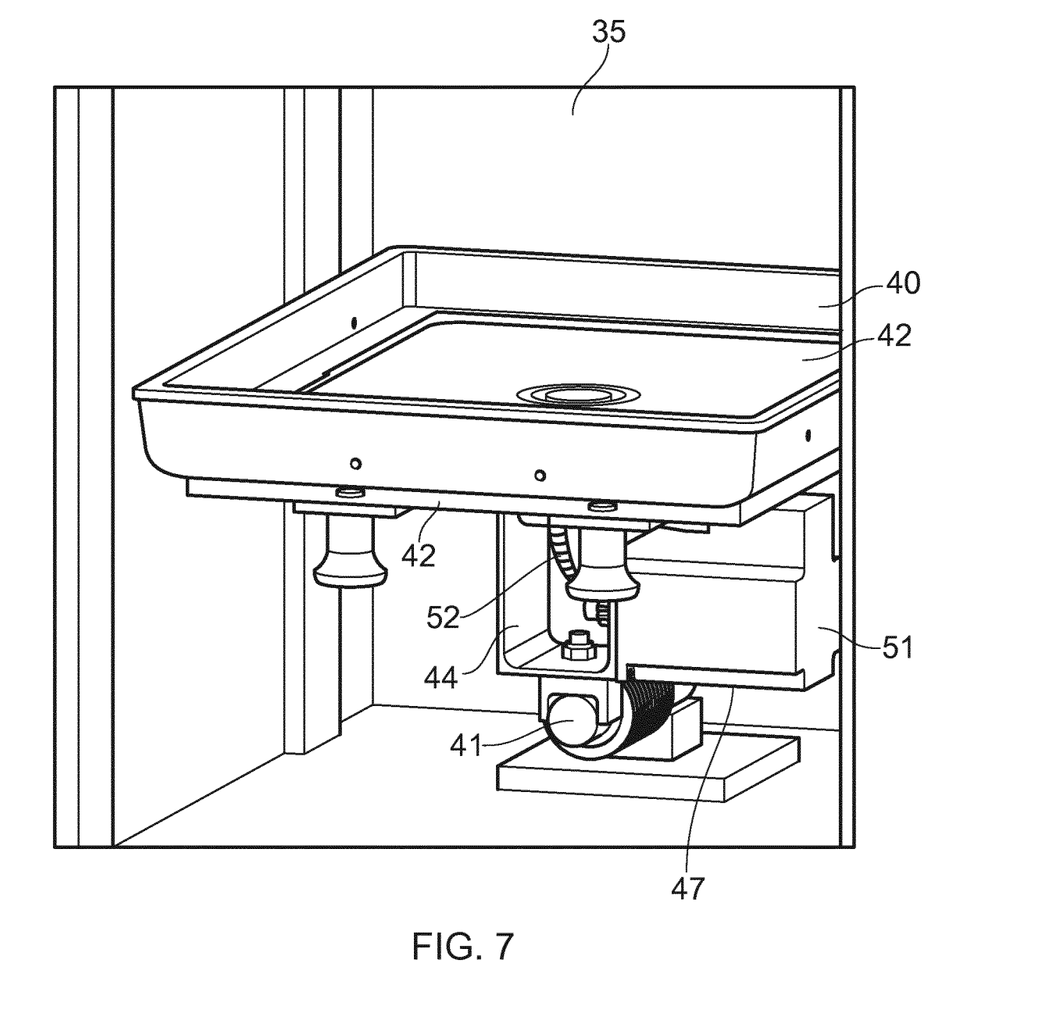
FIG. 7 shows an enlarged partial view of the apparatus shown in FIGS. 1 and 2.

FIG. 7 shows the rocking mechanism in more detail view from the front, door, side of the instrument looking into the main chamber 35 with the cover plate 21 removed. A stepper motor 51 of the rocking mechanism 47 is shown as well as a reduction pinion gear pair 52 driven by the stepper motor and driving the plate support 44 to rotate back and forth. In this view a load sensor, in the form of a load cell 41 is visible which in use is used to measure the quantity of fluid added or removed from the bioreactor, and cell culture control.

Figure 8:
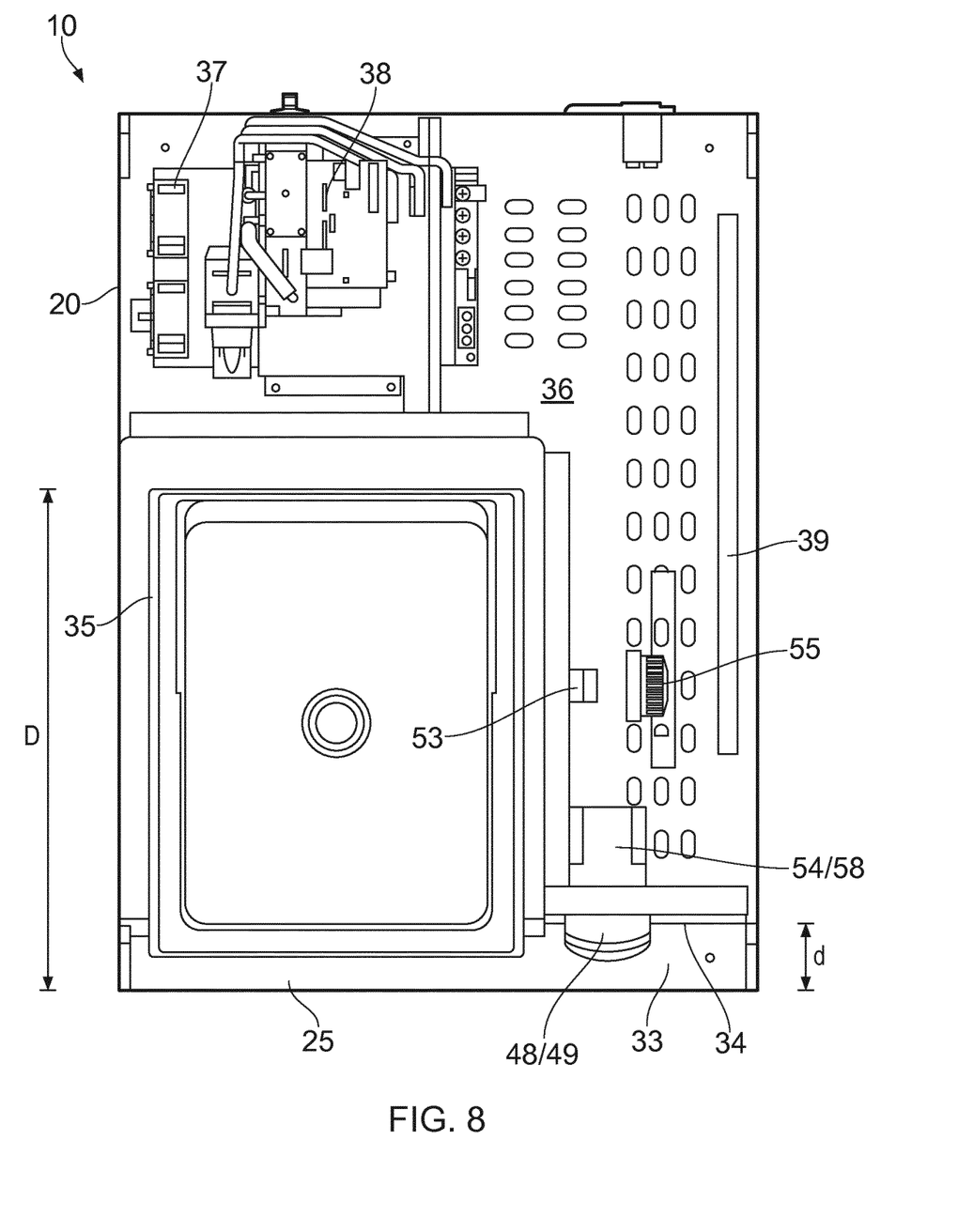
FIG. 8 shows a sectional plan view of the apparatus shown in FIGS. 1 and 2.

FIG. 8 shows a sectional view through the instrument 10 looking down such that the main chamber 35 is visible having a depth D from front to back, as well as the antechamber 33, which has a much shallower depth d. In the remaining region 36 of the housing is separated from the chambers 35/33 and encloses electrical and electronic control components which are kept way from possible leaks from the bioreactor and can be kept at lower temperature than the main chamber, so that electrical parts will have a longer life. In addition, cleaning of the electrical parts can be avoided because they are separated from the chambers 35/33. In more detail, those electrical/electronic components include a power supply 37, a perfusion gas supply control unit 38, a control circuit board 39, a chamber air heater 53, pump head 48/49 drive motors 54/58, a single board computer 55 and various connecting wires and conduits not shown.

Figure 9:
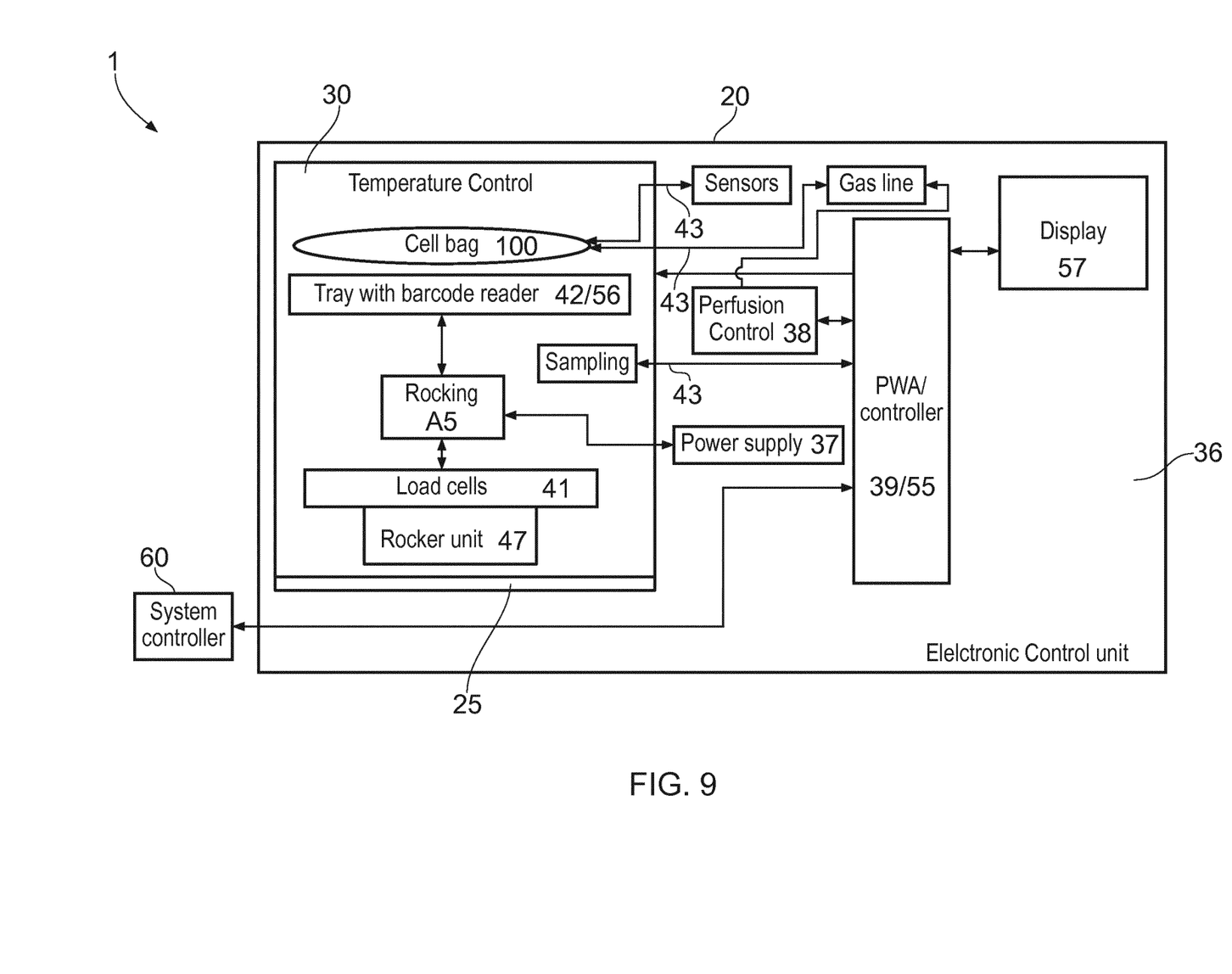
FIG. 9 shows a schematic representation of the functioning of the apparatus shown in FIGS. 1 and 2.

FIG. 9 shows schematic block diagram of the functioning of the instrument 10, with references relating to the physical components mentioned above and illustrated in the previous Figures. In use the flexible bag bioreactor 100 (cell bag) is preferred, and is loaded into the chamber 30 as detailed above. Connections 43 are made and the door 25 is closed. The tray 42, in this embodiment includes a bar code reader 56, to reader a bar code from the bag and relay the identity of the bag to a controller 39/55. Other identification means are possible, for example an RFID transducer could be used, embedded in the cell bag 100. The identity of the bag will determine the appropriate cell culture regime, and additional, external information can be sought by the controller via a system controller 60, for example the target cell density required. Having determined the appropriate cell culture regime, the controller will, typically, control the temperature external to the bag, and optimise the parameters inside the bag. These parameters will vary during the cell culture period, i.e. over a period of up to 28 days, but typically 7 to 21 days. Thus the controller will monitor and adjust the internal pH of the cell culture, the dissolved oxygen content of the fluid in the bag, the weight of the bag to determine the amount of fresh fluid introduced and the amount of waste fluid withdrawn from the bag. Sampling of these parameters and the cell density is performed automatically. A continuous perfusion regime is preferred although other known regimes, such as a fed batch regime could be used. Conveniently, a display 57 is incorporated into the door 25, and the door includes a window which is darkened to reduce light entering the chamber or has a shutter, openable to view the chamber 30 through the window, but closable to reduce or exclude light in normal operation of the instrument.

In use the instrument will function as a stand-alone system using the display 57 to output status information, along with other stand-alone instruments where plural instruments are employed, meaning that no external control is required for the operation of the instrument or instruments. However, it is possible that the system controller 60 can be used, will function either to simply supply information relating to the requirements of the cell bag loaded in the instrument, or additionally monitor plural instruments, or with suitable software, to monitor and control each instrument, so that internal instrument control is dominant. The then subordinate controller 39/55 of each instrument can take back instrument control if communication with the system controller is lost. The communication between the instruments and the system controller is preferably a system BUS link for example a universal serial bus of know configuration, but a wireless link is possible, for example as specified by IEEE802.11 protocols operating at 0.9 to 60 GHz. It is envisaged that each instrument will be automatically recognised by software running on the system controller, without the need for any user input.

Once the cell culture is complete, as determined by sampling and or cell bag weight, it is removed from the instrument and used for its intended purpose, for example autologous cell therapy. Where it is the biomolecules produced by cultured cells that is of interest these can be removed when the cell bag is emptied, or they can be removed from the filtrate extracted from the bag during culturing. The chamber 30 is easily cleaned ready for the next bag to be introduced, with minimal down-time. Thus it is apparent that the instrument described above allows convenient loading and unloading of disposable bioreactors, and can be closely spaced in stacked rows so that the density of instruments is about 4 to 6 per metre squared when viewed from the instruments' front faces. A typical bioreactor 100 for use with the instrument 10, will be small by present day standards, i.e. approximately 50 millilitres and 2500 millilitres, and so the system described above is a small scale system, having multiple cell culture instruments, which are each readily accessible and controllable, and optimise the available space.

Although embodiments have been described and illustrated, it will be apparent to the skilled addressee that additions, omissions and modifications are possible to those embodiments without departing from the scope of the invention claimed.

The invention claimed is:

1. A biomanufacturing apparatus, comprising:
a housing including top and bottom faces which allow stacking of plural housings;
an access door at a front side of the housing;
a substantially enclosed bioreactor chamber inside the housing accessible via the door, wherein the substantially enclosed bioreactor chamber comprises a single main chamber and a single antechamber, wherein the antechamber is shallower in depth than the main chamber relative to the door; and
a further substantially enclosed region inside the housing containing at least one of electrical parts and electronic control components,
wherein the main chamber houses;
a single tray for supporting a bioreactor, and
a single tray support including a mechanism for rocking the tray in use,
wherein the antechamber houses a panel mounting at least a fluid handling portion of at least one fluid pump device,
wherein the at least the fluid handling portion of the at least one fluid pump device projects beyond the panel and into the antechamber, and
wherein the substantially enclosed bioreactor chamber houses at least one connection for connecting to at least one of conduit and path for carrying at least one of fluids, gas, and electricity.

2. The apparatus of claim 1, wherein the tray support further includes a sliding portion for sliding the tray at least partially out of the chamber via the open door.

3. The apparatus of claim 1, wherein said at least one connection is mounted to the panel, said at least one connection being adapted for removably connecting one or more of: a gas conduit; a pH sensor connection path; and a dissolved oxygen sensor connection path.

4. The apparatus of claim 1, wherein the tray is at least one of slideable relative to and removable from, the tray support.

5. The apparatus of claim 4, wherein the door includes a further tray support for supporting a tray on the door when the door is open, the further support being collapsible to allow the door to close.

6. The apparatus of claim 1, wherein the rocking tray support includes a load sensor operable to determine the mass supported on the tray.

7. The apparatus of claim 1, further including a bioreactor heater mounted at the tray for conductive heating of the bioreactor, and a chamber air heater for convective heating the gaseous atmosphere in the chamber, each heater being controlled by a temperature control.

8. The apparatus of claim 1, wherein said top and bottom faces are generally flat and include height adjustable feet.

9. The apparatus of claim 1, further including a support external to the housing to one side of the door for supporting at least one of consumable materials and fluid products.

10. The apparatus of claim 3, further including a bioreactor in the form of flexible bag supported on the tray, said bag including fluid conduits passing via said fluid handling portions and paths connected or connectable to said connections.

11. The apparatus of claim 10, wherein the bioreactor has a capacity of between approximately 50 millilitres and 2500 millilitres.

12. The apparatus of claim 1, wherein the tray or tray support includes a reader for recognising the identity of a bioreactor mounted on the tray.

13. The apparatus of claim 1, wherein the chamber, with the door closed, reduces or substantially excludes visible light.

14. The apparatus of claim 1, wherein the access door includes a status display viewable from at least one of the outside of the door and a window for viewing the chamber.

15. A biomanufacturing system comprising a plurality of stacked biomanufacturing apparatus of claim 1, in data communication with a central computer including software operable to at least one of monitor the status of and control one or more of the apparatus.

16. The apparatus of claim 9, wherein the at least one of consumable materials and fluid products comprise at least one of bagged waste and biomolecules.

17. A method of loading or unloading the apparatus of claim 1, the method comprising the steps of:
   a) opening the door of the housing;
   b) partially sliding out the tray of the housing;
   c) loading a bioreactor onto the tray or unloading a bioreactor from the tray;
   d) connecting or disconnecting the conduits and paths; and
   e) closing the door.

* * * * *